(12) United States Patent
Jensen et al.

(10) Patent No.: US 7,522,701 B2
(45) Date of Patent: Apr. 21, 2009

(54) SYSTEM AND METHOD FOR IMAGE COMPOSITION USING POSITION SENSORS

(75) Inventors: Vernon Thomas Jensen, Draper, UT (US); Richard Leparmentier, Salt Lake City, UT (US); Vianney Pierre Battle, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 287 days.

(21) Appl. No.: 11/314,681

(22) Filed: Dec. 20, 2005

(65) Prior Publication Data

US 2007/0140427 A1    Jun. 21, 2007

(51) Int. Cl.
*G01N 23/04* (2006.01)

(52) U.S. Cl. .................. 378/62; 378/98.12; 378/162; 382/130

(58) Field of Classification Search ............. 378/98.9, 378/98.11, 98.12, 62, 162, 163; 382/130, 382/132
See application file for complete search history.

(56) References Cited

U.S. PATENT DOCUMENTS

| | | | | |
|---|---|---|---|---|
| 6,944,265 B2* | 9/2005 | Warp et al. | ............... | 378/98.12 |
| 6,961,406 B2* | 11/2005 | Hayashi | ................... | 378/98.12 |
| 2002/0176541 A1 | 11/2002 | Schubert et al. | | |
| 2005/0033149 A1 | 2/2005 | Strommer et al. | | |
| 2005/0245807 A1 | 11/2005 | Boese et al. | | |

* cited by examiner

*Primary Examiner*—Jurie Yun
(74) *Attorney, Agent, or Firm*—The Small Patent Law Group; Dean D. Small

(57) ABSTRACT

Certain embodiments of the present invention provide systems and methods for image composition. Certain embodiments include acquiring a first image of an object using an imager, obtaining first positional information for the imager with respect to the object, acquiring a second image of the object using the imager, obtaining second positional information for the imager with respect to the object, and creating a composed image using the first and second images. A spatial relationship between the images is maintained using the positional information. A composed image may be created by constructing a memory map of image data related to the object and inserting the images into the memory map based on the positional information, for example. A composed image may be created by combining the images based on the positional information, for example.

27 Claims, 9 Drawing Sheets

FIG. 4
Spatial Image Measurement
Acquisition
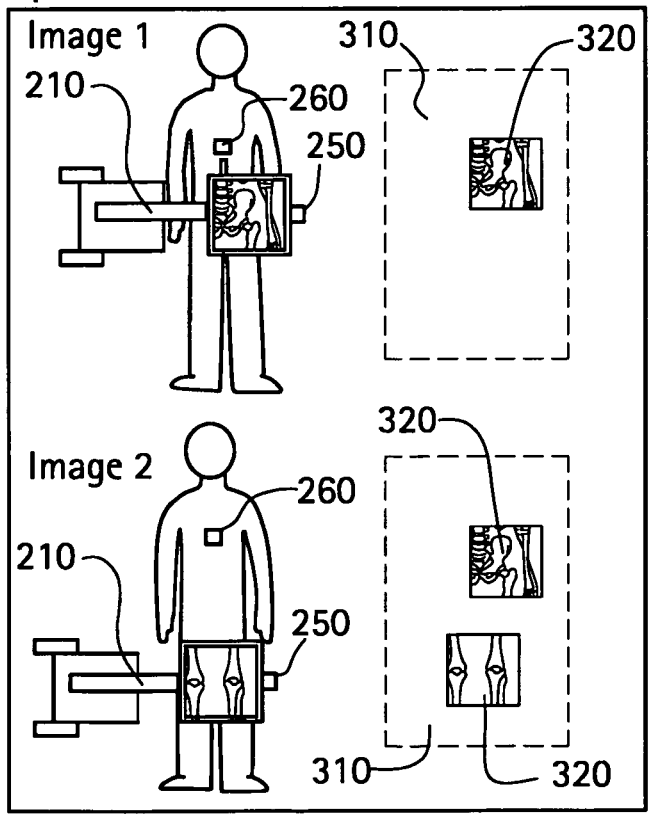
Measurement / Display
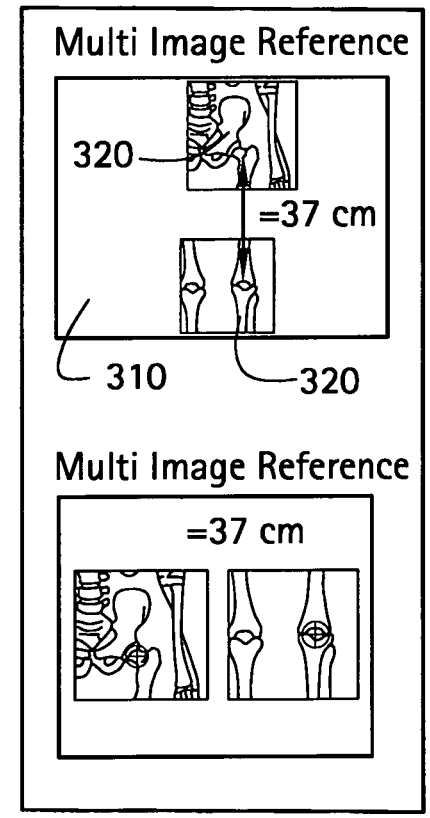

FIG. 7
Masks
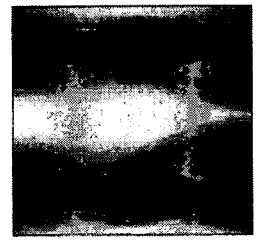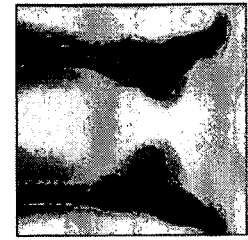
Injected & subtracted images
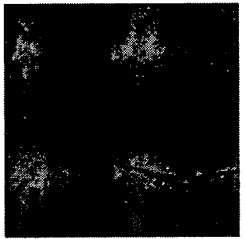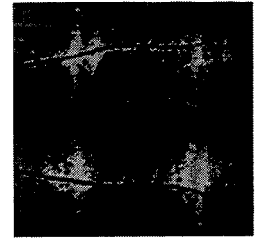
Pasted image

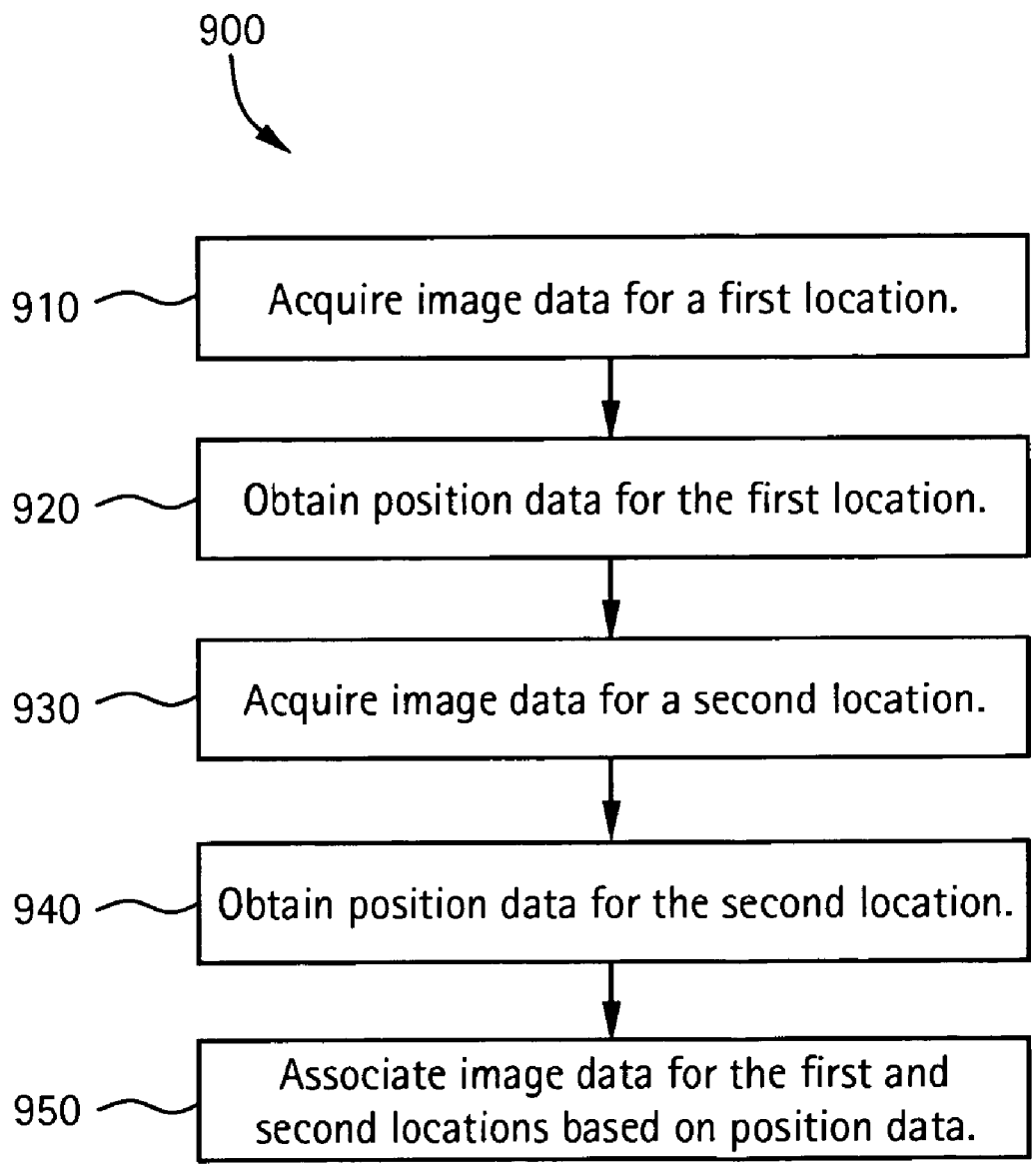

SYSTEM AND METHOD FOR IMAGE COMPOSITION USING POSITION SENSORS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to x-ray imaging. In particular, the present invention relates to a system and method for compound x-ray imaging using position sensors.

Digital imaging systems may be used to capture images to assist a doctor in making an accurate diagnosis. Digital radiography and/or fluoroscopy imaging systems typically include a source and a detector. Energy, such as x-rays, produced by the source travel through an object to be imaged and are detected by the detector. An associated control system obtains image data from the detector and prepares a corresponding diagnostic image on a display.

The detector may be a flat panel detector, such as an amorphous silicon flat panel detector, for example. Alternatively, the detector may be an image intensifier or other detecting device, for example. Historically, image intensifier systems produce much distortion. However, current techniques are being used to correct distortion in image intensifier images. For example, passive (e.g., markers in an image) and/or active (e.g., shielding) techniques are being applied to reduce distortion.

Image data obtained from a detector may be used for diagnosis and treatment of diseases and other ailments. For example, Digital Subtraction Angiography (DSA) is an x-ray imaging technique used by interventional radiologists and surgeons to diagnose and treat vascular diseases and conditions. 'Roadmap' and 'Subtract' are two functions commonly found on mobile and fixed interventional x-ray systems. A fundamental principal of DSA is to subtract one image from another in order to focus attention on image differences. In a typical 'Roadmap' sequence, a 'mask' image is subtracted from subsequent frames of video. The mask image is acquired while radio-opaque dye contrast is present in a vascular system. Since the dye contrast is not present in subsequent frames, a resultant DSA image shows only the areas where dye contrast was present in the mask. Since other anatomic features were present in the mask and in subsequent frames, the other anatomic features will 'subtract out', leaving only a 'roadmap' of the vascular system.

One of the challenges with DSA is to maintain registration between the subtraction pair of images. Even small misregistration due to patient respiration, or c-arm mechanical instability can have a significant negative effect on the resultant image. Although some systems have software features that allow automatic, or manual mask re-registration, re-registration is only practical when solving for small misalignments.

In addition current implementations of DSA require the mask and the subsequent fluoroscopic imaging sequence to be acquired without moving the imaging system with respect to the patient. This lack of movement constrains a region where DSA may be used or requires acquiring new masks each time the imaging system is moved with respect to the patient.

Mobile C-arm systems have become a standard tool for x-ray imaging in intraoperative surgical procedures. Mobile C-arm systems provide x-ray imaging used for successful intervention in a wide variety of surgical interventions. The mobility and relative low cost of mobile C-arm systems make mobile C-arm systems a more flexible imaging solution compared with much larger, more expensive 'fixed room' systems.

Although mobile C-arms are becoming more sophisticated in order to meet the needs of new and emerging intervention methods, there are some performance limitations that are constrained by the need to maintain mobility. Compared to a fixed-room system, one such constraint is an inability to link the C-arm and operating table positions and geometries as a single mechanical gantry system.

Image processing techniques, such as 'image tiling' and 'image stitching', are commonly used in digital photography and are also used by 'fixed-room' x-ray systems to expand contiguous image views beyond the limitations normally imposed by image receptor size. These processes are most efficiently achieved when patient position may be determined and/or controlled in relationship to an x-ray image detector.

X-ray fluoroscopy may be used with a contrast dye to perform vascular run-off studies, for example. A contrast dye may be injected into a patient, and a radiologist obtains a series of images from the abdominal aorta into the iliac artery and/or into the left or right leg, for example. As the dye contrast is injected, the C-arm imager is manually moved to follow the day in fluoroscopic imaging. Alternatively, dye may be injected in a first area covered by an x-ray detector to obtain images of the first area. Then, the C-arm is moved to a second area and another dye contrast injection is made to obtain images of the second area. The injection and repositioning process may be repeated until desired images are obtained. Thus, a system and method for improved dye contrast fluoroscopic imaging would be highly desirable. A system and method which minimize an amount of contrast injected in a patient would be highly desirable.

Therefore, there is a need for an improved method and system for compound imaging. There is a need for a system and method for compound x-ray imaging using position sensors. Additionally, there is a need for a system and method for improved image tiling using positional information.

BRIEF SUMMARY OF THE INVENTION

Certain embodiments of the present invention provide systems and methods for image composition. Certain embodiments of a method include acquiring a first image of an object using an imager, obtaining first positional information for the imager with respect to the object, acquiring a second image of the object using the imager, obtaining second positional information for the imager with respect to the object, and creating a composed image using the first image and the second image. A spatial relationship between the first image and the second image is maintained using the first positional information and the second positional information.

In an embodiment, the first image is acquired in a first fluoroscopic imaging mode, and the second image is acquired in a second fluoroscopic imaging mode. The first fluoroscopic imaging mode may be a no dye contrast mode, for example, and the second fluoroscopic imaging mode may be a dye contrast injection mode, for example.

In an embodiment, a composed image may be created by constructing a memory map of image data related to the object and inserting the first image and the second image into the memory map based on the first positional information and the second positional information, for example. In an embodiment, a composed image may be created by combining the first image and the second image based on the first positional information and the second positional information, for example.

In an embodiment, the method further includes generating a subtraction mask based on at least one of the first image and the second image and at least one of the first positional information and the second positional information. In an embodiment, the method further includes measuring a distance in at least one of the first image and the second image based on at least one of the first positional information and the second positional information.

Certain embodiments provide a method for spatial alignment of a plurality of images. The method includes obtaining positional data for an image acquisition device relative to an object being imaged and registering a plurality of images in spatial alignment in a virtual image map based at least in part on the positional data. The method may further include using positional data to control image acquisition. Furthermore, the method may include correcting an image perspective based at least in part on the positional data. In an embodiment, image landmarks in the plurality of images may be used to assist in image alignment and/or image perspective correction, for example. In an embodiment, position feedback may be provided based on the positional data for positioning the image acquisition device for image exposure.

In an embodiment, a composed image may be created by inserting the plurality of images into the virtual image map based on the positional data. In an embodiment, digital subtraction angiography may be performed based on the plurality of images and the positional second positional data. A composed image may be created by combining the plurality of images based on positional data, for example.

Certain embodiments provide an image processing system for generating a composed image. The system includes an image processor generating an image map based on image data from a plurality of images and positional data associated with each of the plurality of images. Image data for each of the plurality of images is positioned in the image map according to the positional data to form a spatially aligned composed image. The plurality of images may include images from one or more modalities, for example.

In an embodiment, the image processor facilitates digital subtraction angiography using the image data and the positional data. In an embodiment, the image processor provides feedback for positioning an image acquisition device based on the positional data and the image data. In an embodiment, the image processor is configured to obtain spatial measurements in the composed image based on the image data and the positional data.

Certain embodiments provide a computer-readable medium including a set of instructions for execution on a computer. The set of instructions includes a positioning routine configured to obtain positional data for an image acquisition device relative to an object being imaged. The set of instructions also includes a registration routine configured to register a plurality of images in spatial alignment in a virtual image map based at least in part on the positional data.

BRIEF DESCRIPTION OF SEVERAL VIEWS OF THE DRAWINGS

FIG. 4 shows acquisition and measurement of image data used in accordance with an embodiment of the present invention.

FIG. 7 shows an example of a plurality of image slices that may be integrated into a single larger image in accordance with an embodiment of the present invention.

FIG. 9 illustrates a flow diagram for a method for image composition used in accordance with an embodiment of the present invention.

Figure 1:
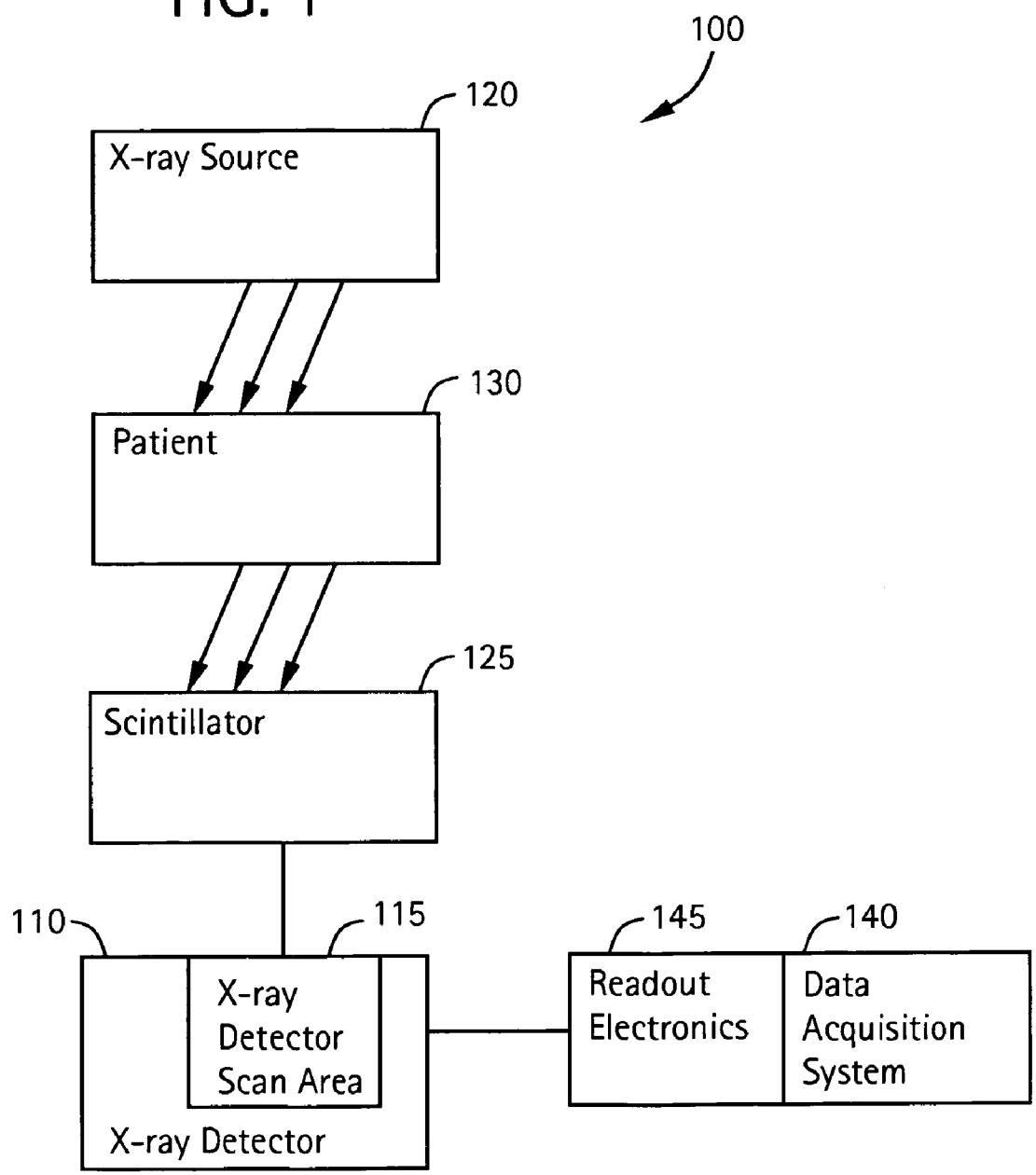
FIG. 1 illustrates an imaging system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an imaging system 100 used in accordance with an embodiment of the present invention. The imaging system 100 includes a plurality of subsystems. For the purposes of illustration, the imaging system 100 is described as an x-ray system. The imaging system 100 includes subsystems, such as an x-ray detector 110 including an array 115 of detector cells, an x-ray source 120, a scintillator 125, and an object 130. The imaging system 100 also includes a data acquisition system 140 with read out electronics 145. In an embodiment, the scintillator 125 comprises a screen positioned in front of the detector 110. In an embodiment, the detector 110 is an amorphous silicon flat panel detector. The object 130 may be a patient or another object to be imaged.

The object 130 is positioned in imaging system 100 for imaging. In one exemplary system, an x-ray source 120 is positioned above the object 130. The x-ray detector 110 is positioned below the object 130. The scintillator 125 is positioned between the object 130 and the x-ray detector 110. X-rays are transmitted from the x-ray source 120 through the object 130 to the scintillator 125. The scintillator 125 emits light in response to the x-rays transmitted from the x-ray source 120 through the object 130. The emitted light is transmitted to the x-ray detector 110 and the x-ray detector array 115. For example, light emitted by the scintillator 125 activates or discharges photodiodes in the detector array 115 to varying degrees. The read out electronics 145 may include a reference and regulation board (RRB) or other data collection unit. The RRB may accommodate and connect data modules to transfer data from the detector 110 to the data acquisition system 140. The read out electronics 145 transmit the data from the detector 110 to the data acquisition system 140. The data acquisition system 140 forms an image from the data and may store, display, and/or transmit the image. Preprocessing and processing functions may be applied to the acquired image before and/or after storage, display, and/or transmission, for example.

Figure 2:
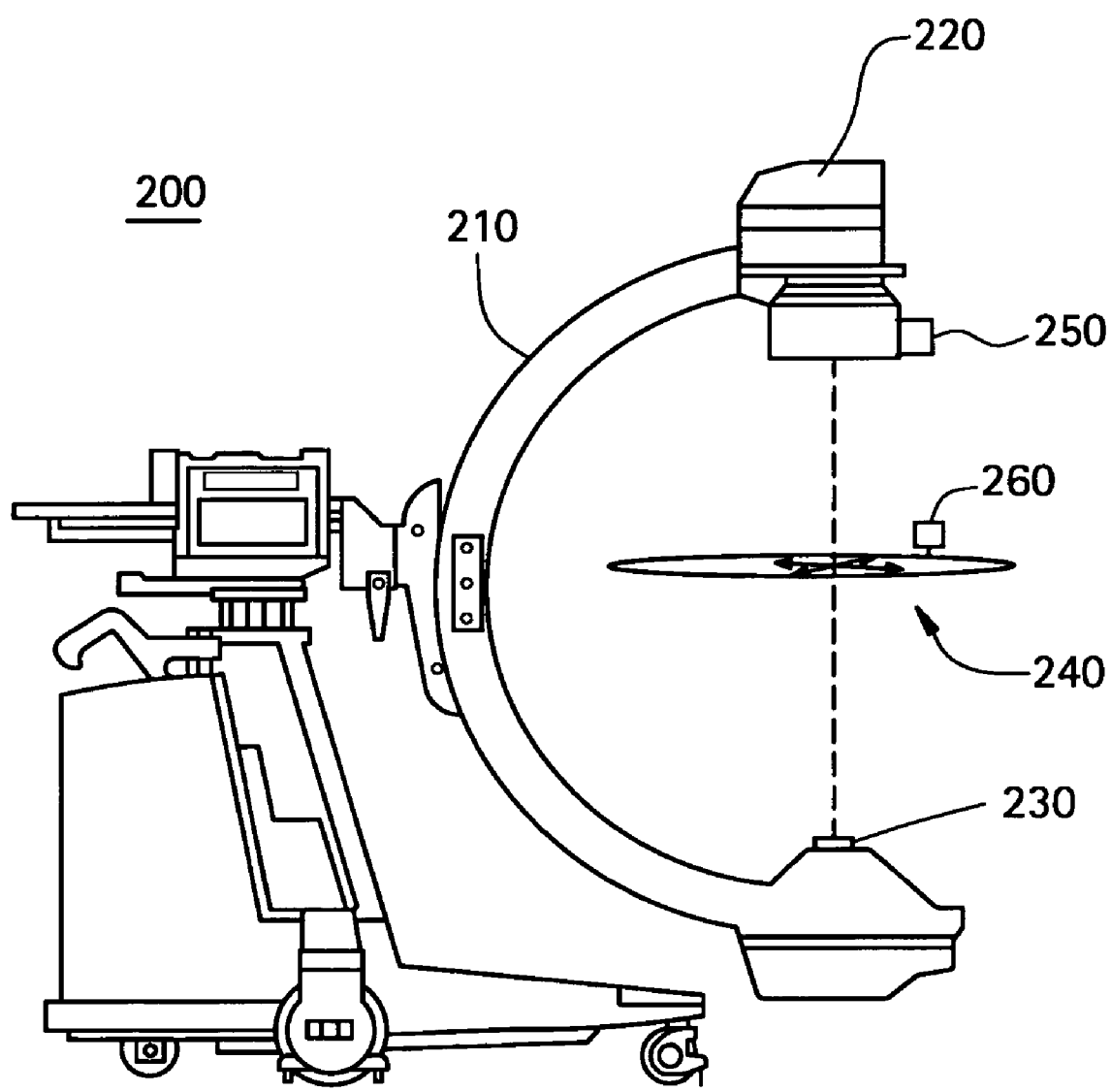
FIG. 2 illustrates a C-arm imaging system used in accordance with an embodiment of the present invention.

The imaging system 100 may be implemented as a fixed or mobile imaging system, for example. FIG. 2 illustrates a C-arm imaging system 200 used in accordance with an embodiment of the present invention. The C-arm system 200 may include the imaging system 100 or similar system, for example. The C-arm system 200 includes a C-arm 210, an energy source 220 (e.g., an x-ray energy source), an image acquisition device 230 (e.g., a detector or camera), a positioning surface 240 (e.g., a patient positioning table), a C-arm tracking device 250, and an object or table tracking device 260. In an embodiment, the C-arm 210 may be an L-arm, an O-arm, a C-gantry, and/or other positioning element aside from a traditional C-arm, for example.

In an embodiment, an object may be positioned on the positioning surface 240. Image data related to the object may be obtained at the image acquisition device 230 after energy from the energy source 220 has irradiated the object. Additionally, position and/or other tracking data may be obtained from the C-arm tracking device 250 and the object/table tracking device 260. Image and position data may be processed using a processor associated with the image acquisition device 230 and/or a separate processing unit, for example.

Certain embodiments provide a system and method for utilizing positional tracking technology to create and maintain a 'composed' two-dimensional (2D) on a single plane or a plurality of 2D data sets on multiple planes or a three-dimensional (3D) image. The composed image may be used in several contexts, including Digital Subtraction Angiography (DSA), whether in regular subtraction mode or roadmapping, for example. In an embodiment, 2D images and 3D images from one or more modalities may be registered and combined in a composed 2D or 3D image.

First, the composed image is acquired by recording a fluoroscopic ("fluoro") imaging run in a first mode along with obtaining positional information for the imager with respect to the patient. Thus, a composed image is created that is larger than the imager (e.g., detector) size, for example. Next, fluoro images are acquired in a second mode. The knowledge of the imager's position in the second step enables access to fluoro image data at a location in the first mode and derivation of a combination of first and second mode images without having to re-acquire fluoro in the first mode during the second step.

In a DSA scenario, the first mode corresponds to imaging with no dye contrast injected, and the second mode corresponds to imaging with a dye contrast injected. In a 'roadmap' scenario, the first mode corresponds to imaging with a dye contrast injected, and the second mode corresponds to imaging with no dye contrast injected. In the second mode, an accurate subtraction mask may be extracted from the region of the 'composed image that corresponds to the current c-arm position. In an embodiment, mask data may be re-indexed to provide near-real-time (e.g., 30 frames per second) mask updates while panning the c-arm. If the entire composed image memory map is initialized to '0', for example, and if the boundaries of a calculated mask area include 'null' data, then the areas of null data may appear as normal 'live fluoro' after subtraction.

In an embodiment, image re-registration may occur using two images, an image with dye contrast and an image without dye contrast. A mask image may be subtracted from the images. The mask image may be rotated underneath the images to correct for patient motion and minimize an effect of dye contrast difference and mask edges due to patient motion. Thus, a mask may be moved around in memory to remove edges and other effects caused by patient motion between obtained images. In an embodiment, positional information obtained from a composed data set and a live image allows image data to be manipulated similar to re-registration, for example.

In an embodiment, landmarking may be applied to the composed image and/or one or more components of the composed image, for example. In landmarking, a weight of all or part of a mask image may be adjusted. Then, if the mask is set to all zeros, for example, the live image is visible. In contrast, if the mask values are maximized, then the image may be completely subtracted. Thus, by adjusting values or weights within a mask, certain portions of an image may be masked or alternately emphasized, for example. In an embodiment, a user may perform a complete subtraction, no subtraction, or a landmarked subtraction in between with respect to the composed image. The mask may be used, for example, to allow some anatomical structure to remain in the composed image, rather than be subtracted or otherwise masked out.

In an embodiment, image distortion correction may be applied to maintain spatial integrity when fitting data into the composed image space. If the spatial integrity is maintained within the accumulated or composed image, spatial integrity may also be used to measure bones and structures that do not fit into a single image frame. For example, length measurements of a femur may be obtained using two images (proximal and distal).

In many interventional x-ray procedures, an anatomy of interest may be aligned with the x-ray imaging system by moving a positioning table top and/or c-arm, for example. For example, in vascular run-off studies, a physician moves the table top in two dimensions (e.g., X and Y planes) while imaging in order to follow a dye contrast injection from a main artery through peripheral arteries. Thus, a large composed image may be created because x-ray images are acquired over a large area.

In an embodiment, using a reference on the patient, such as the object tracking device 260, and a reference on the C-arm 210, such as the C-arm tracking device 250, data may be collected to create a two or three dimensional image area or map. Tracking devices 250, 260 may be any of a variety of transmitter coils and/or other tracking devices providing positional feedback with respect to a reference coordinate system, for example. Using navigational reference data, a virtual image may be formed showing where the C-arm 210 is relative to the patient or other object. The virtual image or map may include an area larger than an area covered by a single fluoroscopic image. As the C-arm 210 is moved, the virtual image is updated by image data received for an area in the virtual image map. Thus, the virtual image shows areas of obtained image data and areas of unknown image data in which the C-arm 210 has not been positioned to obtain image data.

Figure 3:
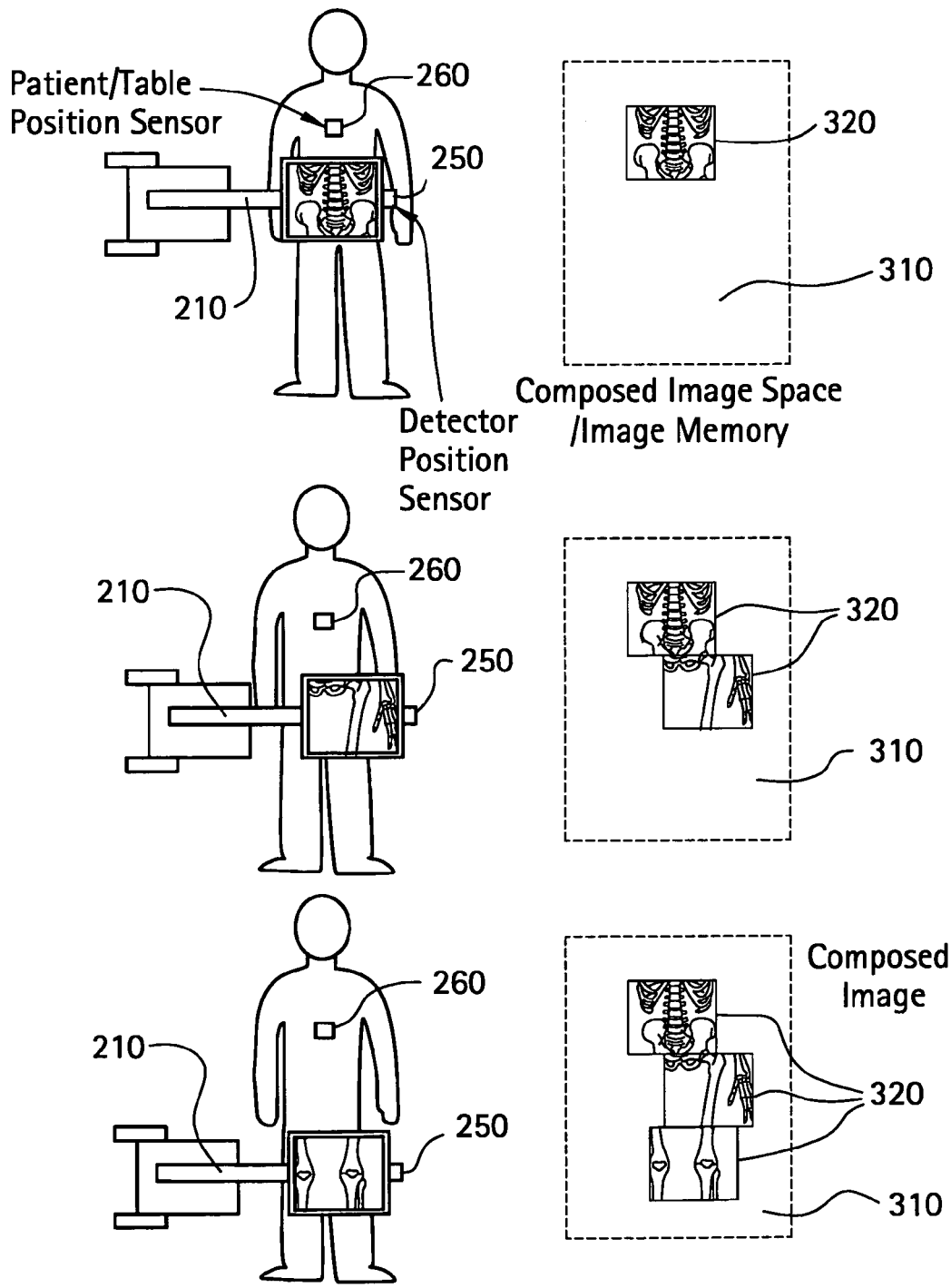
FIG. 3 illustrates a composed image space used in accordance with an embodiment of the present invention.

As illustrated in FIG. 3, a virtual image map or composed image space 310 is generated. As the C-arm 210 is moved, positioning data from the patient tracking device 260 and the C-arm tracking device 250 is collected in conjunction with image data 320 to populate the composed image space 310. As the C-arm 210 is moved along a patient or other object, a compound image occupying the composed image space 310 is completed. Additionally, in an embodiment, old image data may be replaced and/or otherwise updated with new image data if x-ray exposures overlap in the image map 310. For example, newly acquired image data may replace image data residing at the same address in memory for the composed image memory map. In an embodiment, the composed image space 310 remains valid until the navigation component is moved relative to the C-arm 210. Thus, the C-arm 210 may be moved with respect to the patient or other object and the composed image 310 may be dynamically displayed and updated as image data is obtained via the C-arm 210. In an embodiment, the composed image space 310 is a geometrically accurate memory space. In an embodiment, distortion correction may be applied to maintain a correct image geometry.

As shown in FIG. 4, an image of a pelvis may be acquired and related image data 320 added to the memory map 310. Then, an image of a knee may be obtained, and image data from the knee image is added to the memory map 310. Navigational information for the patient and the C-arm 210 is also obtained with each image exposure. Using the navigation information, the knee image may be accurately placed in relation to the pelvis image such that memory addresses in the memory map 310 correspond to an X-Y coordinate measurement value, for example. Additionally, a correlation between spatial measurement and memory address allows a user to measure components of an image, such as a femur, using the image data in the memory map 310. For example, orthopedic procedures may be planned using image data and spatial measurements in the compound image memory map 310. In an embodiment, a user, such as a surgeon or radiologist, may select or "click on" items in the virtual image memory map 310 and determine, manually or automatically, relationships, measurements, etc., related to those items or landmarks.

Figure 5:
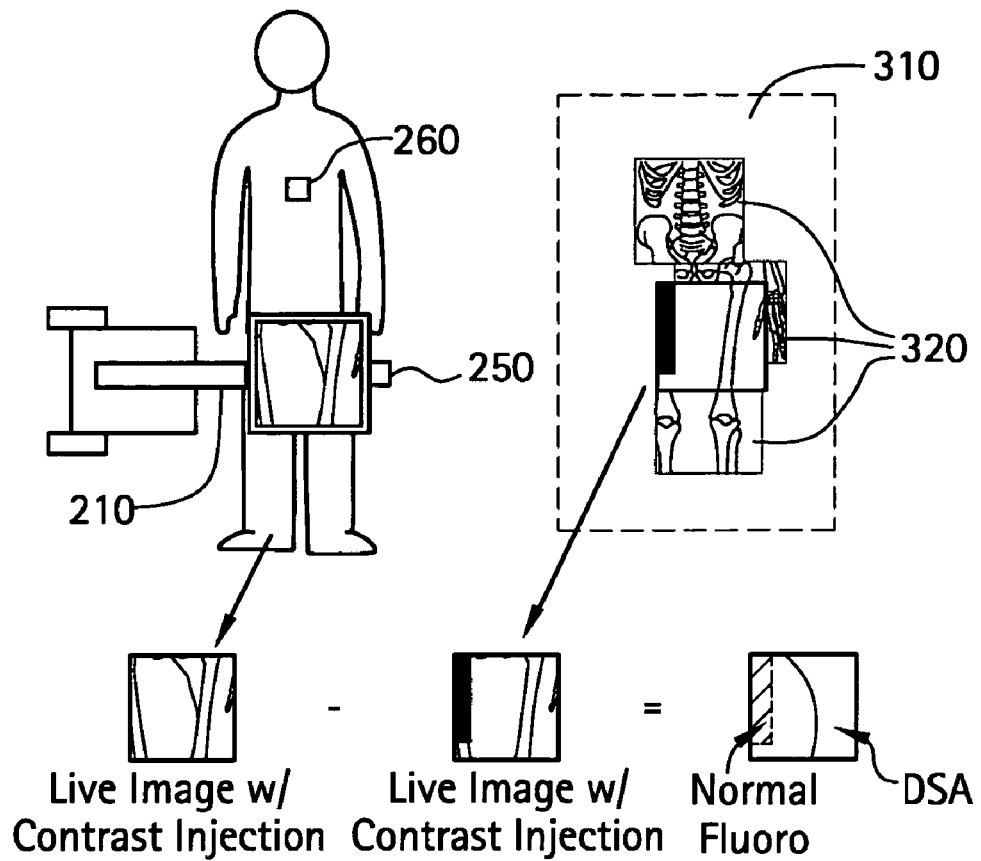
FIG. 5 shows digital subtraction angiography used in accordance with an embodiment of the present invention.

In FIG. 5, the C-arm 210 is panned with respect to the patient and image data 320 is obtained to populate the virtual image map 310. For example, the C-arm 210 may be panned from the bifurcation of the iliac in the patient's mid torso down the left leg to complete data in the composed image area 310. Using the image map 310, dye contrast may be injected into the patient without having to take a first acquisition phase because a virtual mask is stored in memory for C-arm 210 positions.

In an embodiment, fluoroscopic images may be obtained in subtraction mode. Image data 320 available in the composed image 310 may be used as a subtraction mask. Thus, the image map 310 may serve as half of a subtraction image pair. Anatomical information in the composed image 310 may be used for subtraction techniques, for example. Using image data 320 in the composed image virtual map 310, the C-arm 210 may be positioned, and data appearing in an acquired image may be identified based on the map 310. If image data 320 is present in the image map 310, image data 320 may be displayed even when an image is not being acquired. Positional information may also be obtained from the image map 310.

In an embodiment, new image data may be averaged with, substituted for, and/or otherwise combined with image data in the image map. For example, image frames may be averaged using a standard averaging algorithm, a complex averaging algorithm, and/or other process. Frame averaging and/or other processing may reduce noise and provide cleaner images, for example. In an embodiment, peak opacification may be used to process image data in the composed map. As image frame data is received, a new pixel value is compared to an existing value at the pixel location. If the new pixel value is darker than the previous pixel value, the new pixel value replaces the previous pixel value, for example. Otherwise, the existing pixel value may not be replaced. Spatial relationships between acquired image data pixel values may be determined based on positional feedback from the tracking devices 250, 260, for example. Thus, dye contrast may be maintained in the image map. In an embodiment, a dye 'roadmap' may be displayed and analyzed without additional imaging. In an embodiment, a roadmap may be displayed without performing a subtraction.

Thus, certain embodiments reduce a number of scout images obtained to position a c-arm or other imaging equipment. Certain embodiments provide a composed geometric area bigger than an image acquisition device, such as an image intensifier, detector, camera, for example.

In an embodiment, a composed image may be created and maintained with newly acquired data and/or updated data acquired at a location in the composed image already containing data. Information in the composed image may be updated in a variety of ways. For example, old information in the image may be replaced with new information. Alternatively, old information maybe averaged with new information. In another embodiment, peak opacity values may be maintained in the composed image. Alternatively, minimum opacity values may be maintained in the composed image.

In an embodiment, a composed image may be used to enable scouting of a c-arm. Additionally, certain embodiments may be used to create composed images using gamma cameras, infra-red cameras, and/or other imagers, for example. Furthermore, positional data may be used to generate feedback for automatic positioning of a c-arm or other imaging unit by a processor and/or manual positioning by a user, for example.

Certain embodiments reduce x-ray dose by a variety of methods. For example, certain embodiments recycle or reuse imaging data that may otherwise be discarded. Certain embodiments may reduce mask re-acquisition. Alternatively or in addition, certain embodiments reduce scout positioning exposures through use of a composed image. Certain embodiments reduce exposure dosage and improve imaging without precise mechanical re-alignment of a saved mask, for example. Certain embodiments enable DSA on extended regions of interest bigger than the imager without the need to retake masks during DSA. Rather, mask information is collected prior to the DSA run.

Certain embodiments provide a system and method for utilizing position information from a surgical navigation system to facilitate 'image tiling'. In an embodiment, for example, a peripheral vascular 'run-off' study may be performed using a mobile c-arm. A catheter or syringe is used to inject an x-ray opaque contrast agent into peripheral arteries of a patient. Keeping the c-arm stationary, an interventional radiologist manually manipulates a radiolucent 'floating' table top to follow the contrast agent or dye as the contrast agent moves through the arteries to the peripheral regions of the patient's limbs. Vascular occlusions or abnormalities may be diagnosed, treated, and outcomes are verified in this manner. Imaging tiling may be used to analyze image data, such as run-off study data.

Figure 6:
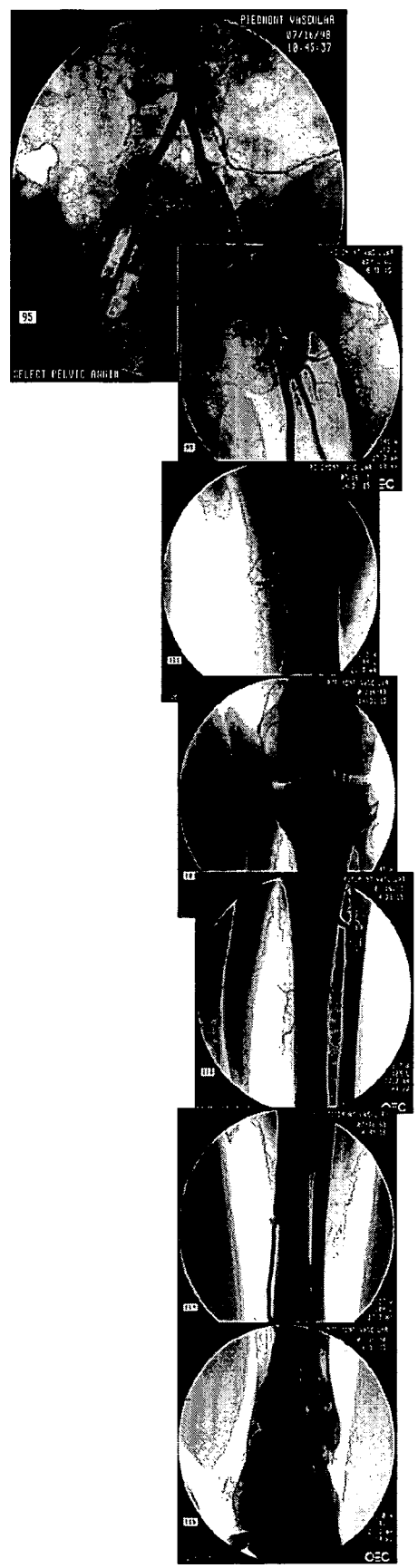
FIG. 6 illustrates an example of a series of image slices obtained from a vascular run-off study in accordance with an embodiment of the present invention.

In an embodiment, several image frames may be combined, or 'stitched' together, to form a seamless aggregate image of a large area. Certain embodiments use surgical navigation or tracking sensors to provide position information to determine a proper alignment and/or spatial correction to fuse images into a composed or tiled image. FIG. 6 illustrates an example of a series of image slices obtained from a vascular run-off study in accordance with an embodiment of the present invention. The image slices or 'tiles' may be combined into a single image, for example.

FIG. 7 shows an example of a plurality of image slices that may be integrated into a single larger image in accordance with an embodiment of the present invention. For example, as shown in FIG. 7, masks may be applied to image slices or frames to isolate the dye contrast injected images. Then the injected and subtracted images may be tiled to form a combined pasted image, as shown in FIG. 7, for example.

X-ray image registration and multiple image 'tiling' may be achieved with the use of x-ray opaque (or semi-opaque) fiducial markers, for example. Dynamic position feedback may be used in conjunction with fiducial markers to efficiently synchronize x-ray acquisition with a table, patient, and/or c-arm system. Other registration and distortion correction methods may also be used in conjunction with certain embodiments to augment image tiling. For example, x-ray opaque markers and/or patterns as well as anatomical feature-based or markerless distortion correction may be used to improve image tiling. In an embodiment, further automation may be achieved using navigation position information to control table motion (e.g., with a motorized table), and/or c-arm motion (e.g., with a motorized c-arm system such as the GE OEC Series 9800 MD). Certain embodiments may also be used to extend an area of contiguous acquisition of 3D fluoro imaging, for example.

Certain embodiments acquire both image data and positional/navigation data from c-arm and patient sensors. A series of image slices, such as a series of image exposures obtained as the c-arm is moved, may include a plurality of perspectives, for example. That is, perspective may change within the multiple images. Tracking information from the c-arm and patient sensors may provide information regarding differing perspectives in image slices. Positional information allows images from different planes and/or perspectives to be tiled or otherwise combined into a composite image, for example. Positional information may help reduce distortion introduced by tiling image slices, for example. In an embodiment, measurement of an object in a composed image and/or image processing, such as DSA, may be performed using a tiled image similar to the systems and methods described above.

Certain embodiments provide image views that are not constrained by image receptor size. Certain embodiments may also reduce an x-ray exposure to a patient and to interventional health care providers who work in close proximity to the x-ray system. X-ray exposure may be reduced using position information from navigation sensors for efficient x-ray acquisition, for example. Certain embodiments may be implemented on both 'fixed-room' and mobile imaging systems, such as mobile c-arm x-ray imaging systems.

In an embodiment, x-ray dose may also be optimized by optimizing image acquisition. In one example, application software may provide a human interface (graphic or other) that assists in positioning of a table, patient, and/or c-arm in order to accomplish maximum coverage of an area of interest using a minimal number of x-ray images. Additionally, certain embodiments may be automated by triggering x-ray acquisition based on relative positioning, for example.

Thus, certain embodiments use navigation or tracking sensors to register multiple two dimensional and/or three dimensional images to be spatially aligned. In certain embodiments, sensors may also be used to control x-ray acquisition, for example. In an embodiment, navigation sensor and position information is factored into image perspective correction calculations. In an embodiment, image landmark(s) (e.g., fiducial and/or anatomical) may be used to assist in image alignment and/or perspective correction, for example. In an embodiment, navigation sensor position feedback (e.g., graphical, audible, etc.) is provided to an operator for manual positioning of a mobile c-arm for x-ray image exposure. In an embodiment, position feedback is used to automatically drive table and/or c-arm positioning for x-ray image exposure. Positional and image information allow return to a previous position for further imaging, for example.

Figure 8:
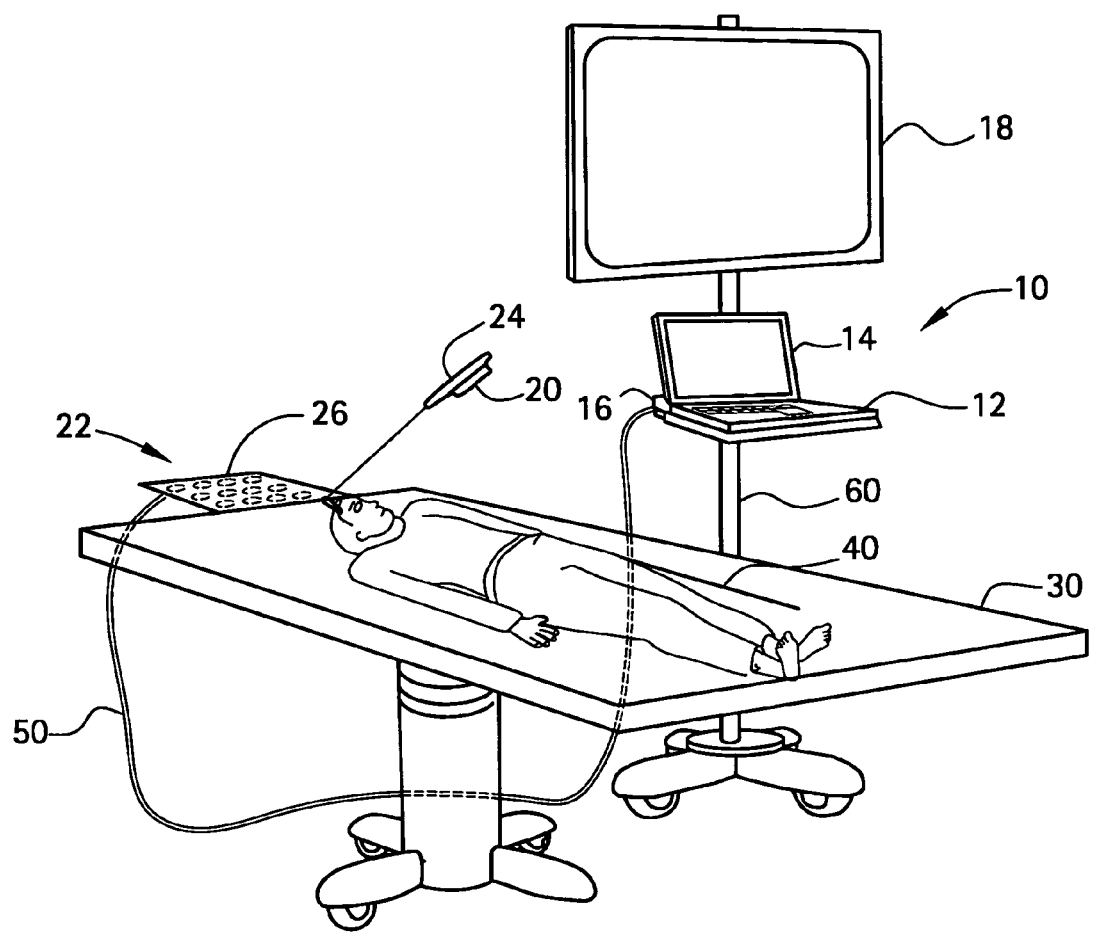
FIG. 8 illustrates an exemplary medical navigation system that may be used with certain embodiments of the present invention.

In certain embodiments, a navigation/tracking system works in conjunction with an imaging system to provide positional information that may be used in image composition, for example. FIG. 8 illustrates an exemplary medical navigation system 10 that may be used with certain embodiments of the present invention. The navigation system 10 includes a portable computer 12, a display 14, and a navigation interface 16. The medical navigation system 10 is configured to operate with an electromagnetic field generator 20 and electromagnetic sensor 22 to determine the location of a device 24. The navigation system 10 may also be configured to determine the location of tracking devices 250 and/or 260, for example.

A table 30 is positioned near the electromagnetic sensor 22 to support a patient 40 during a surgical procedure. In an embodiment, the table 30 may be the positioning surface 240, for example. A cable 50 is provided for the transmission of data between, the electromagnetic sensor 22 and the medical navigation system 10. Alternatively, data may be transmitted between the sensor 22 and system 10 via a wireless communication medium, for example. The medical navigation system 10 may be mounted on a portable cart 60 and/or stationary, for example. The system 10 may be in communication with a second display 18, for example.

The electromagnetic sensor 22 may be a printed circuit board, for example. Certain embodiments may include an electromagnetic sensor 22 comprising a printed circuit board receiver array 26 including a plurality of coils and coil pairs and electronics for digitizing magnetic field measurements detected in the printed circuit board receiver array 26. The magnetic field measurements may be used to calculate the position and orientation of the electromagnetic field generator 20 according to any suitable method or system. After the magnetic field measurements are digitized using electronics on the electromagnetic sensor 22, the digitized signals are transmitted to the navigation interface 16 through cable 50. The medical navigation system 10 is configured to calculate a location of the device 24 based on the received digitized signals.

FIG. 9 illustrates a flow diagram for a method for image composition used in accordance with an embodiment of the present invention. At step 910, a first set of image data is acquired for a first location on an object, such as a patient, being imaged. For example, a slice or snapshot of a patient leg, a pelvis, a chest, etc., may be scanned by an imager, such as a detector on a C-arm. At step 920, first position data is obtained for the object in relation to the imager. For example, positional data of a C-arm at a first position (e.g., over the patient's chest) with respect to a patient may be obtained using a tracking device or other sensor.

At step 930, a second set of image data is acquired for the object (e.g., a patient) at a second location. For example, an additional image exposure may be obtained for the same or a different area of the patient. At step 940, second position data is obtained for the object with respect to the imager. As above, position data for the C-arm at a second position with respect to the patient may be obtained using a tracking device and/or other sensor, for example.

Then, at step 950, the first and second sets of image data are associated based on the first and second position data. For example, positional data showing a spatial relationship between two images or sets of image data may be used to place the two images within a virtual map of the image space. Alternatively, positional data showing a spatial relationship between two images or sets of image data may be used to tile or stitch together the two images into one composite image. Positional data may allow images to be combined or stored in a composite image map while improving geometric accuracy and reducing distortion, for example.

In an embodiment, positional data for an image acquisition device relative to an object being imaged may be used to register images in spatial alignment in the virtual image map. In an embodiment, positional data may be used to control image acquisition, such as by affecting position of the image acquisition device. In an embodiment, image perspective may be corrected/adjusted based on positional data and other information, for example. Image landmarks (e.g., fiducials and/or anatomy) in one or more images to assist in image alignment and/or perspective correction, for example. In an embodiment, position feedback may be provided based on positional data to aid in automatic and/or manual positioning of the image acquisition device for image exposure, for example. Certain embodiments construct a 2D composed image set and/or multiple 2D composed image sets which allow a user to return to a C-arm oblique position and then move in the x and y coordinate planes to obtain image data, for example.

Embodiments of the above systems and methods may be implemented in a variety of ways. Embodiments of the above systems and methods may be implemented as a set of instructions on a computer-readable medium, for example. Embodiments of the above systems and methods may be implemented using an image processor, for example. The image processor may be implemented in software, hardware, and/or firmware, for example. The image processor may be a separate processor and/or may be integrated with and/or substitute for another processor in an imaging system or image review system, for example. The image processor may be a processor in an imaging system or image review system programmed to perform functions of the above-described systems and methods, for example.

Thus, certain embodiments provide methods and systems for subtraction and roadmapping in digital subtract angiography using a composite image map. Certain embodiments allow landmarking for variable masking of data in an image. Certain embodiments allow spatial filtering through updating and/or replacing pixel values in a composite image map using a variety of methods including averaging and peak opacity, for example. Certain embodiments provide feedback for detector or other image acquisition device positioning such as by marker centering and combined image position. Additionally, certain embodiments allow for spatial measurements, such as measurements in a multi-image and/or combined image reference. Furthermore, certain embodiments facilitate multi-modality image registration and fusion, such as 2D to 2D, 2D to 3D, and/or 3D to 2D multi-modality registration and fusion.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for image composition, said method comprising:
    constructing a memory map of image data related to an object, wherein the memory map at least initially comprises an area of unknown image data;
    acquiring a first image of the object using an imager;
    obtaining first positional information for said imager with respect to said object;
    acquiring a second image of said object using said imager;
    obtaining second positional information for said imager with respect to said object; and
    creating a composed image by inserting said first image and said second image into said memory map based on said first positional information and said second positional information, wherein a spatial relationship between said first image and said second image is maintained using said first positional information and said second positional information.

2. The method of claim 1, wherein said first image is acquired in a first fluoroscopic imaging mode and wherein said second image is acquired in a second fluoroscopic imaging mode.

3. The method of claim 2, wherein said first fluoroscopic imaging mode comprises a no dye contrast mode, and wherein said second fluoroscopic imaging mode comprises a dye contrast injection mode.

4. The method of claim 1, further comprising generating a subtraction mask based on at least one of said first image and said second image and at least one of said first positional information and said second positional information.

5. The method of claim 1, further comprising measuring a distance in at least one of said first image and said second image based on at least one of said first positional information and said second positional information.

6. A method for spatial alignment of a plurality of images, said method comprising:
    obtaining positional data for an image acquisition device relative to an object being imaged;
    creating a virtual image map based on said positional data; and
    registering a plurality of images in spatial alignment in the virtual image map based at least in part on said positional data, wherein the virtual image map at least initially comprises an area of unknown image data.

7. The method of claim 6, further comprising using said positional data to control image acquisition.

8. The method of claim 6, further comprising correcting image perspective based at least in part on said positional data.

9. The method of claim 6, further comprising using image landmarks in said plurality of images to assist in at least one of image alignment and image perspective correction.

10. The method of claim 6, further comprising providing position feedback based on said positional data for positioning said image acquisition device for image exposure.

11. The method of claim 6, further comprising creating a composed image by inserting said plurality of images into said virtual image map based on said positional data.

12. The method of claim 6, further comprising performing digital subtraction angiography based on said plurality of images and said positional data.

13. The method of claim 6, further comprising creating a composed image by combining said plurality of images based on said positional data.

14. An image processing system for generating a composed image, said system comprising:
an image processor generating a virtual image map based on image data from a plurality of images and positional data associated with each of said plurality of images,
wherein the virtual image map at least initially comprises an area of unknown image data and image data for each of said plurality of images is positioned in said virtual image map according to said positional data to form a spatially aligned composed image.

15. The system of claim 14, wherein said image processor facilitates digital subtraction angiography using said image data and said positional data.

16. The system of claim 14, wherein said image processor provides feedback for positioning an image acquisition device based on said positional data and said image data.

17. The system of claim 14, wherein said plurality of images include images from one or more modalities.

18. The system of claim 14, wherein said image processor is configured to obtain spatial measurements in said composed image based on said image data and said positional data.

19. A computer-readable medium including a set of instructions for execution on a computer, said set of instructions comprising:
a positioning routine configured to obtain positional data for an image acquisition device relative to an object being imaged; and
a registration routine configured to register a plurality of images in spatial alignment in a virtual image map based at least in part on said positional data, wherein the virtual image map at least initially comprises an area of unknown image data.

20. A method of imaging a patient using an imaging system, said method comprising:
generating a composed image comprising a plurality of images of the patient acquired on the same 2D plane, the images being spatially related with respect to each other wherein the composed image size is larger than the imaging system detector size;
acquiring a first image of a region of interest of the patient included in the composed image and associated imaging system positional data;
generating a subtraction image of the region of interest using the composed image and the acquired first image and associated imaging system positional data; and
measuring a distance from a point in the first image to a point in a second image noncontiguous with the first image using the associated imaging system positional data of the first and second images.

21. A method in accordance with claim 20 further comprising:
acquiring a third image of a region of interest of the patient included in the composed image and associated imaging system positional data; and
generating a subtraction image of the region of interest using the composed image and the acquired third image and associated imaging system positional data.

22. A method in accordance with claim 20 wherein generating a composed image comprises injecting the patient with a radio-opaque dye.

23. A method in accordance with claim 20 wherein acquiring an image of a region of interest comprises injecting the patient with a radio-opaque dye.

24. A method in accordance with claim 20 wherein generating a composed image comprises maintaining a spatial relationship between the plurality of images in the composed image using associated imaging system positional data for each image.

25. An imaging system comprising:
an energy source configured to radiate energy toward a detector through an examination area;
a patient support extending at least partially into the examination area;
a tracking device configured to ascertain the relative positions of said energy source and said patient support with respect to a coordinate system;
an imaging processor configured to generate a composed image comprising a plurality of images acquired using the detector and respective positional data for each image received from the tracking device, wherein said imaging processor is configured to generate a memory map of image data relating to the patient wherein the memory map comprises a plurality of acquired images of the patient, navigational data associated with each image, and addresses for the images and data, the memory map at least initially comprising an area of unknown image data.

26. An imaging system in accordance with claim 25 wherein said energy source is an x-ray source coupled to said detector through a C-arm.

27. An imaging system in accordance with claim 25 wherein said patient support is configured to translate in at least two dimensions.

* * * * *